United States Patent [19]
Vander Wielen et al.

[11] Patent Number: 4,720,415
[45] Date of Patent: Jan. 19, 1988

[54] COMPOSITE ELASTOMERIC MATERIAL AND PROCESS FOR MAKING THE SAME

[75] Inventors: Michael J. Vander Wielen; Jack D. Taylor, both of Roswell, Ga.

[73] Assignee: Kimberly-Clark Corporation, Neenah, Wis.

[21] Appl. No.: 760,437

[22] Filed: Jul. 30, 1985

[51] Int. Cl.⁴ ............................................. D06N 7/04
[52] U.S. Cl. ............................ 428/152; 156/163; 156/164; 156/183; 156/290; 428/198; 428/284; 428/286; 428/287; 428/297; 428/298; 428/903
[58] Field of Search ............... 428/156, 170, 171, 172, 428/198, 296, 284, 286, 287, 340, 903, 152; 156/163, 164, 183, 290

[56] References Cited
U.S. PATENT DOCUMENTS

| | | | |
|---|---|---|---|
| 1,544,312 | 6/1925 | Grey | 428/177 |
| 1,911,227 | 5/1933 | Galligan | 154/2 |
| 2,022,852 | 12/1935 | Galligan | 154/33 |
| 2,030,746 | 2/1936 | Galligan | 154/2 |
| 2,125,495 | 8/1938 | French | 154/2 |
| 2,343,374 | 3/1944 | Hargreaves | 2/237 |
| 2,401,830 | 6/1946 | Kahil | 28/77 |
| 2,559,649 | 7/1951 | Little | 428/198 |
| 2,905,581 | 9/1959 | Maxey | 428/198 |
| 2,957,512 | 10/1960 | Wade | 428/198 |
| 3,316,136 | 4/1967 | Pufahl | 156/160 |
| 3,468,748 | 9/1969 | Bassett | 161/122 |
| 3,622,434 | 11/1971 | Newman | 156/183 |
| 3,644,157 | 2/1972 | Draper | 156/160 |
| 3,673,026 | 6/1972 | Brown | 156/181 |
| 3,687,797 | 8/1972 | Wideman | 161/129 |
| 3,694,815 | 10/1972 | Burger | 2/270 |
| 3,828,367 | 4/1973 | Bollrgeois | 128/169 |
| 3,842,832 | 10/1974 | Wideman | 128/169 |
| 3,849,241 | 11/1974 | Butin | 264/210 F |
| 3,868,729 | 3/1975 | Lynam | 2/237 |
| 3,873,403 | 3/1975 | Edelman | 161/76 |
| 4,081,301 | 3/1978 | Buell | 156/164 |
| 4,100,324 | 7/1978 | Anderson | 428/288 |

(List continued on next page.)

FOREIGN PATENT DOCUMENTS 2260716  5/1974  Fed. Rep. of Germany .

OTHER PUBLICATIONS

Shell Tech. Bulletin SC:38-82, Kraton G 1650.
Shell Tech. Bulletin SC:70-83, Kraton D 1101.
Shell Document SC:68-85, Typical Properties 1985.
Shell Tech. Bulletin SC:39-85, Kraton G 1652.
Shell Tech. Bulletin SC:763-83, Kraton DX 1117.
Shell Tech. Bulletin SC:607-84, Kraton GX 1657.
Shell Tech. Bulletin SC:606-84, Kraton D 1116.
Shell Tech. Bulletin SC:605-82, Kraton DX 1112.
Shell Tech. Bulletin SC:604-82, Kraton D 1111.
Shell Document SC:455-81, Kraton, Processing & Fabricating Kraton Thermoplastic Rubber Compounds.

Primary Examiner—James J. Bell
Attorney, Agent, or Firm—Joseph P. Harps

[57] ABSTRACT

A method of producing a composite elastic material comprises stretching an elastic web to elongate it, for example, elongating a nonwoven web of meltblown elastomeric fibers, and bonding the elongated web to at least one gatherable web, such as a spunbonded polyester fiber material, under conditions which soften at least a portion of the elastic web to form the bonded composite web of elastic material. The composite material is relaxed immediately after the bonding to prevent the elastic web from losing its ability to contract from the stretched dimensions which it assumed during the bonding step. Such immediate relaxation of the composite material after the bonding step results in the elastic web retaining its ability to contract so that, upon termination of the elongating force, the elastic web contracts to form gathers in the gatherable web. The bonding may be effectuated by pattern embossing overlaid elastic and gatherable webs with at least portions of the elastic web heated to at least its softening temperature. The resultant composite elastic material comprises a coherent elastic web which is bonded to at least one coherent gatherable web whereby the gatherable web is extensible and contractible with the elastic web upon stretching and relaxing of the composite material.

44 Claims, 3 Drawing Figures

U.S. PATENT DOCUMENTS

| | | | |
|---|---|---|---|
| 4,209,563 | 6/1980 | Sisson | 428/288 |
| 4,259,220 | 3/1981 | Bunnelle | 525/98 |
| 4,297,157 | 10/1981 | Van Vliet | 156/163 |
| 4,305,970 | 12/1981 | Kelly | 428/220 |
| 4,323,534 | 4/1982 | Des Marais | 264/176 R |
| 4,333,782 | 6/1982 | Pieniak | 156/164 |
| 4,340,563 | 7/1982 | Appel | 264/518 |
| 4,355,425 | 10/1982 | Jones | 2/402 |
| 4,397,645 | 8/1983 | Buell | 604/380 |
| 4,413,623 | 11/1983 | Pieniak | 604/365 |
| 4,418,123 | 11/1983 | Bunnelle | 428/517 |
| 4,426,420 | 1/1984 | Likhyani | 428/288 |
| 4,430,086 | 2/1984 | Repke | 128/284 |
| 4,446,189 | 5/1984 | Romanek | 428/152 |
| 4,450,026 | 10/1983 | Pieniak | 604/365 |
| 4,525,407 | 6/1985 | Ness | 428/138 |
| 4,543,099 | 9/1985 | Bunnelle | 156/164 |
| 4,606,964 | 8/1986 | Wideman | 428/152 |

COMPOSITE ELASTOMERIC MATERIAL AND PROCESS FOR MAKING THE SAME

BACKGROUND OF THE INVENTION

1. Field of the Invention

The present invention is concerned with an elasticized material, a method of making the same and articles made therefrom. More particularly, the present invention is concerned with a composite elastic material comprising at least one elastic web, such as a nonwoven web of elastomeric fibers, bonded to one or more webs of gatherable material, such as one or more webs of a nonwoven, non-elastic material.

2. Description of the Related Art

Composite fabrics comprising at least one layer of nonwoven textile fabric mechanically secured to an elastic layer are known. For example, U.S. Pat. No. 4,446,189 discloses textile laminate materials comprising an inner layer of elastic material, such as a polyurethane foam of a thickness of about 0.025 inches, needle punched at a plurality of locations to a nonwoven textile fabric layer. The needle punched superposed layers are then stretched within the elastic limits of the elastic layer to permanently stretch the nonwoven fabric layer material needle punched thereto. When the elastic layer is allowed to relax and return to substantially its condition prior to being stretched, the nonwoven fabric layer is stated to exhibit increased bulk by virtue of the relaxation of its permanently stretched fibers.

U.S. Pat. No. 4,209,563 discloses a method of making an elastic material which includes continuously forwarding relatively elastomeric fibers and elongatable but relatively non-elastic fibers onto a forming surface and bonding at least some of the fiber crossings to form a coherent cloth which is subsequently mechanically worked, as by stretching, following which it is allowed to relax. As described by the patentee at column 8, line 19 et seq, the elastic modulus of the cloth is substantially reduced after the stretching, resulting in the permanently stretched non-elastic filaments relaxing and looping to increase the bulk and improve the feel of the fabric (column 9, lines 9–14 and FIG. 3). Forwarding of the filaments to the forming surface is positively controlled, which the patentee (column 7, line 19 et seq) contrasts to the use of air streams to convey the fibers as used in meltblowing operations. Bonding of the filaments to form the coherent cloth may utilize embossing patterns or smooth, heated roll nips, as set forth at column 9, line 44 et seq.

U.S. Pat. No. 3,316,136 discloses a composite fabric comprising a layer of an elastic or resilient material and an overlaying layer of fabric, for example, a woven fabric. The elastic fabric may be a polyurethane foam or a nylon woven to impart stretchability or the like and, as is disclosed in the paragraph bridging columns 1 and 2 of the patent, an adhesive may be applied in a predetermined pattern to the elastic material which is then stretched, and while in a stretched or elongated state, the overlying fabric is contacted therewith and held in pressure engagement for a time sufficient to ensure adhesion of the two layers. When the applied adhesive is dry, tension on the backing material is released causing the overlying non-elastic fabric to gather in the areas outlined by the adhesive.

U.S. Pat. No. 3,687,797 discloses the manufacture of a resilient cellulosic wadding product attained by laminating paper and a prestretched polyurethane foam material. An adhesive is applied in a desired pattern as illustrated in the drawings and the paper is laminated to either side of the prestretched polyurethane foam material. The paper layers may be wet to reduce their resistance to being compressed by retraction of the prestretched polyurethane foam after lamination of the paper layers thereto, thereby providing a creped effect as illustrated in FIGS. 3 and 4 of the patent.

U.S. Pat. No. 2,957,512 concerns a method of producing elastic composite sheet materials and discloses that a reticulated, fibrous web formed of an elastomeric material such as rubber, including butadiene-styrene copolymers, may be utilized as the elastic ply of a composite material, as disclosed at column 3, lines 18–24. At column 5, lines 39–48, the patent discloses, with reference to FIG. 7 of the drawings, that a relaxed sheet material ply may have a fibrous web of elastomeric material of smaller area than the sheet material stretched so as to conform it in area to the area of the sheet material and the plies bonded together at spaced points or areas. Upon allowing the fibrous elastomeric ply to relax, the composite body is stated to assume the structure shown in FIG. 7, which is described at column 5, line 15 et seq as showing a fibrous web of elastomeric material 50 bonded at spaced areas or lines 56 to a ply 55 of a creped or corrugated flexible sheet material, which may be paper or a synthetic resin material. The structures of the patented invention are stated to be particularly well suited for the manufacture of foundation garments, bathing garments, elastic stockings, ankle braces, belts, garters, galluses and the like.

U.S. Pat. No. 4,426,420 discloses hydraulically entangled spunlaced fabrics and a method of making them which includes (see the Example, column 6) drawing a potentially elastomeric fiber, and allowing it to relax between the draw and wind-up steps.

SUMMARY OF THE INVENTION

In accordance with the present invention there is provided a method of producing a composite elastic material comprising at least one gatherable web bonded to at least one elastic web, the method comprising (a) tensioning an elastic web (which may comprise a fibrous web such as a nonwoven web of elastomeric fibers, e.g., meltblown elastomeric fibers) to elongate it; (b) bonding the elongated elastic web to at least one gatherable web under conditions which soften at least portions of the elastic web to form a bonded composite web; and (c) relaxing the composite web immediately after the bonding step whereby the gatherable web is gathered to form the composite elastic material. Other aspects of the invention provide for maintaining the fibrous elastic web in a stretched condition during bonding, at an elongation of at least about 25 percent, preferably about 25 percent to over 500 percent, for example, about 25 percent to 550 percent elongation during the bonding.

In another aspect of the present invention, the method includes bonding the elongated elastic web to the gatherable web by overlaying the elastic and gatherable webs and applying heat and pressure to the overlaid webs, for example, by heating bonding sites on the elastic web to a temperature of from at least about 65° C. to about 120° C., preferably from at least about 70° C. to about 90° C.

In accordance with the present invention there is also provided an elastic composite material comprising an elastic web bonded to at least one gatherable web which is extensible and contractible with the elastic web upon stretching and relaxing of the composite material, the elastic composite material being made by a method as described above.

In accordance with another aspect of the present invention, the elastic web is bonded to the gatherable web at a plurality of spaced-apart locations in a repeating pattern and the gatherable web is gathered between the bonded locations.

Other aspects of the invention provide that the elastic web may comprise a nonwoven web of elastomeric fibers, preferably elastomeric microfibers, such as, for example, an elastomeric nonwoven web of meltblown elastomeric fibers or an elastomeric film.

Other aspects of the invention include one or more of the following in any combination: the elastomeric fibers, preferably meltblown elastomeric fibers, may be formed from material selected from the group including (i) A-B-A' block copolymers wherein A and A' may be the same or different endblocks and each is a thermoplastic polymer endblock or segment which contains a styrenic moiety such as polystyrene or polystyrene homologs, and B is an elastomeric polymer midblock or segment, e.g., a midblock selected from the group including poly(ethylene-butylene), polyisoprene and polybutadiene, with poly(ethylenebutylene) being preferred and (ii) blends of one or more polyolefins with the A-B-A' block copolymers of (i) where B is a poly(ethylene-butylene) midblock; each of the A and A' endblocks may be selected from the group consisting of polystyrene and polystyrene homologs, e.g., poly(alpha methylstyrene), and where the elastomeric fibers are formed from a blend of one or more polyolefins with an A-B-A' block copolymer where B is a poly(ethylene-butylene) midblock, the polyolefin is selected from one or more of polyethylene, polypropylene, polybutene, ethylene copolymers, propylene copolymers and butene copolymers; the elastomeric film and the elastomeric fibers which form the elastomeric nonwoven web, e.g., the meltblown microfibers, are composed of at least 10 percent, for example at least 20 percent, more specifically at least 30 percent, e.g., from about 10 percent to 90 percent by weight, of the aforesaid A-B-A' block copolymers and greater than 0 percent by weight, e.g., from about 90 percent to about 10 percent by weight, of the polyolefin; the elastic web, e.g., a fibrous elastic web, is bonded to the gatherable web at a plurality of spaced-apart locations in a repeating pattern and the gatherable web is gathered between the bonded locations; the elastic web preferably has a low basis weight of from about 5 to about 300, preferably from about 5 to about 200, grams per square meter (gm/m²), for example, from about 5 to about 100 grams per square meter, although its basis weight can be much higher; the gatherable web is a nonwoven, non-elastic material, preferably one composed of fibers formed from materials selected from the group including polyester fibers, e.g., poly(ethylene terephthalate) fibers, polyolefin fibers, polyamide fibers, e.g., nylon fibers, cellulosic fibers, e.g., cotton fibers, and mixtures thereof. Alternatively, the gatherable web may be any suitable woven fabric.

In one aspect of the invention, the composition of the A-B-A' polymer used is such that the sum of the molecular weight of A with the molecular weight of A' is from about 14 to 31 percent (from about 14 to 29 percent when B is poly(ethylene-butylene)) of the molecular weight of the A-B-A' block copolymer.

Other aspects of the invention are described in the description of preferred embodiments.

DESCRIPTION OF THE PREFERRED EMBODIMENTS

The composite elastic materials of the invention generally comprise at least one layer or web of elastic material bonded to one or more other layers of gatherable material, the elastic web being maintained in a stretched condition within its elastic range during the bonding step so that upon contracting or recovering after release of the stretching, i.e., elongating, tension force, the layer or layers to which it is bonded will gather or pucker. The resultant composite material is itself elastic, any of its non-elastic layers being able to move with the stretching of the elastic layer by reason of the play or give provided by the gathers formed, upon relaxation of the stretched elastic web, in the non-elastic layers to which the non-elastic web or webs are bonded. Composite materials made in accordance with the invention have shown remarkably good uniformity, hand, bulk, strength and elastic properties.

A wide variety of materials may be employed as the elastic web. As used herein and in the claims, the terms "elastic" and "elastomeric" have their usual broad meanings. However, for purposes of this invention "elastic" may be conveniently defined as follows. A material is elastic if it is stretchable to an elongation of at least about 25 percent of its relaxed length, i.e., can be stretched to at least about one and one-quarter times its relaxed length, and upon release of the stretching force will recover at least about 40 percent of the elongation, i.e., will, in the case of 25% elongation, contract to an elongation of not more than about 15 percent. For example, a 100 centimeter length of material will, under the foregoing definition, be deemed to be elastic if it can be stretched to a length of at least about 125 centimeters and if, upon release of the stretching force, it contracts, in the case of being stretched to 125 cm, to a length of not more than about 115 centimeters. Of course, many elastic materials used in the practice of the invention can be stretched to elongations considerably in excess of 25 percent of their relaxed length, and many, upon release of the stretching force, will recover to their original relaxed length or very close thereto. At least for some purposes of the present invention, elastic materials which upon release of the stretching force recover all or nearly all of their elongation are preferred. Elastic webs suitable for use in the invention include both elastic films and nonwoven fibrous elastic webs such as, for example, meltblown elastomeric fibrous webs. Such fibrous webs usually comprise "microfibers", which terms, as used herein and in the claims, means and includes fibers of a diameter not greater than about 100 microns, e.g., fibers of from about 1 to 50 microns in diameter, such as those which may be obtained by the meltblowing and spunbonding processes. In fact, nonwoven webs of meltblown microfibers constitute a preferred embodiment thereof. As used herein and in the claims, "meltblown" microfibers refer to small diameter fibers, usually of a diameter not greater than about 100 microns, made by extruding a molten thermoplastic material as molten threads through a plurality of orifices into a high velocity gas (e.g., air) stream which entrains the extruded threads at their point of emergence from the orifices and attenuates the threads of molten thermoplastic material to reduce the diameter thereof, the gas stream-borne fibers then being deposited upon a collecting screen to form a coherent web of randomly dispersed fibers. Such a process is disclosed, for example, in U.S. Pat. No. 3,849,241, issued Nov. 19, 1974 to Robert R. Butin et al, the disclosure of this patent is hereby incorporated by reference herein.

The fibrous elastic web may also comprise a composite material in that it may be comprised of two or more individual coherent webs or it may comprise one or more webs individually comprised of a mixture of elastic and non-elastic fibers. As an example of the latter type of elastic web, reference is made to the aforementioned U.S. Pat. No. 4,209,563 in which elastomeric and non-elastomeric fibers are co-mingled to form a single coherent web of randomly dispersed fibers. Another example of such a composite web would be one made by a technique such as disclosed in U.S. Pat. No. 4,100,324 issued July 11, 1978 to Richard A. Anderson et al, and assigned to the assignee of this application. That patent discloses a nonwoven material comprised of a mixture of meltblown thermoplastic and other fibers which are combined in the gas stream in which the meltblown fibers are borne so that an intimate entangled co-mingling of thermoplastic meltblown fibers and other fibers, e.g., wood pulp or staple fibers, occurs prior to collection of the fibers upon a collecting device to form a coherent web of randomly dispersed fibers. The disclosure of U.S. Pat. No. 4,100,324 is also incorporated by reference herein.

Useful materials for making the elastomeric fibers of the fibrous elastic web of the present invention, for example, for forming meltblown elastomeric fibers which can be collected to form an elastomeric fibrous nonwoven web which can be utilized in practicing the present invention, are block copolymers having the general formula A-B-A' where A and A' are each a thermoplastic polymer endblock which contains a styrenic moiety such as a poly(vinylarene) and where B is an elastomeric polymer midblock such as a conjugated diene or a lower alkene polymer.

As used herein the term "styrenic moiety" means a monomeric unit represented by the formula:

Preferred materials for forming the elastomeric fibrous nonwoven web are ones in which the A and A' endblocks are selected from the group including polystyrene and polystyrene homologs such as poly(alpha methylstyrene) and the B midblock is either polybutadiene, polyisoprene or poly(ethylene-butylene). Materials of this general type are disclosed in U.S. Pat. Nos. 4,333,782, to H. A. Pieniak, 4,323,534 to Des Marais and 4,355,425 to Jones. Similar materials are disclosed in U.S. Pat. No. 4,418,123, issued Nov. 29, 1983 to William L. Bunnelle which describes A-B-A block copolymers having styrenic endblocks A and amorphous intermediate blocks B. Commercially available A-B-A' block copolymers having a saturated or essentially saturated poly(ethylene-butylene) midblock or segment B represented by the formula:

poly(ethylene-butylene)

where x, y and n are positive integers, and polystyrene A and A' endblocks represented by the formula:

polystyrene where n is a positive integer, which may be the same or different for A and A', are sometimes referred to as S-EB-S (polystyrene/poly(ethylene-butylene)/polystyrene) block copolymers, are available under the trademark KRATON G, for example, KRATON G 1650, KRATON G 1652 and KRATON GX 1657 from Shell Chemical Company. KRATON rubber materials are described in detail in a number of Shell Chemical Company publications including one designated SC: 198-83, 7/83 5M. KRATON G 1650 rubber has a weight ratio of polystyrene A and A' endblocks to poly(ethylene-butylene) B midblocks of 28:72; for KRATON G 1652 rubber the weight ratio is 29:71 and for KRATON GX 1657 the weight ratio is 14:86. For example, with respect to the KRATON GX 1657 the sum of the molecular weight of A with the molecular weight of A' is 14 percent of the molecular weight of the A-B-A' block copolymer. These block copolymers are not believed to contain plasticizer oils although they are commercially available in compounded form. The G 1650 and G 1652 block copolymers are available in crumb form and have a specific gravity of 0.91 and a Shore A Hardness of 75. The GX 1657 block copolymer is available in pellet form, has a specific gravity of 0.90 and a Shore A Hardness of 65. KRATON G materials have been found to be satisfactory for meltblowing in essentially pure form at high extrusion temperatures of at least about 290 degrees Centigrade and to be satisfactory for meltblowing at such high temperatures and at even lower temperatures if blended with polyolefin materials which reduce the viscosity of the blend as compared to the viscosity of the pure KRATON G. The A-B-A' block copolymers may be extruded or otherwise formed to produce elastomeric materials, particularly elastomeric films and elastomeric fibers, more particularly, elastomeric microfibers as by meltblowing. The S-EB-S thermoplastic block copolymer material provides a material which, even when containing a rather high content of polyolefin material, provides satisfactory elastic and strength properties.

Other elastomeric resins which may be utilized to form the elastomeric web of the present invention are A-B-A' block copolymers where A and A' are polystyrene endblocks, as defined above, and B is a polybutadiene midblock represented by the following formula:

polybutadiene where n is a positive integer. This material is sometimes referred to as a S-B-S block copolymer and is available from Shell Chemical Company under the trade designation KRATON D; for example, KRATON D 1101, KRATON D 1102 and KRATON D 1116. According to the Shell Chemical Company publications noted above, KRATON D 1101 rubber has a weight ratio of polystyrene A and A' endblocks to the polybutadiene B midblock of 31:69; for KRATON D 1102 rubber the weight ratio is 28:72; for KRATON D 1116 rubber it is 21:79. For example, with respect to the KRATON D 1116 material the sum of the molecular weight of A with the molecular weight of A' is 21 percent of the molecular weight of the A-B-A' block copolymer. These block copolymers are available as porous pellets, have a specific gravity of 0.94 and a Shore A Hardness of 71 for the D 1101 and D 1102 block copolymers and 65 for the D 1116 block copolymer.

Another S-B-S block copolymer material is commercially available under the trade designation Solprene 418 from the Phillips Petroleum Company.

Yet other elastomeric resins which may be utilized to form the elastomeric web of the present invention are A-B-A' block copolymers where A and A' are polystyrene endblocks, as defined above, and B is a polyisoprene midblock where the midblock is represented by the formula:

where n is a positive integer. These block copolymers are sometimes referred to as S-I-S block copolymers and are also available from the Shell Chemical Company under the trade designation KRATON D, for example, KRATON D 1107, KRATON D 1111, KRATON D 1112 and KRATON D 1117. The KRATON D 1107, D 1111, D 1112 and D 1117 block copolymers have respective weight ratios of polystyrene A and A' endblocks to the B midblock of 14:86 (D 1107); 21:79 (D 1111); 14:86 (D 1112) and 17:83 (D 1117). For example, with respect to the Kraton D 1117 the sum of the molecular weight of A with the molecular weight of A' is 17 percent of the molecular weight of the A-B-A' block copolymer. The D 1111 grade is available as a porous pellet having a specific gravity of 0.93 and a Shore A Hardness of 52. The D 1107, D 1112 and D 1117 block copolymers are available as pellets having specific gravities of 0.92 and Shore A Hardness of 37 for D 1107, 34 for D 1112 and 32 for D 1117. Generally, the S-EB-S thermoplastic block copolymers are easier to fabricate into fibers and microfibers than the S-I-S and S-B-S types and, accordingly, are preferred.

Other exemplary elastomeric materials for use in formation of fibrous nonwoven elastic webs or films in the practice of the invention include polyester elastomeric materials such as, for example, those available under the trade designation Hytrel from E. I. DuPont DeNemours & Co., polyurethane elastomeric materials such as, for example, those available under the trademark ESTANE from B. F. Goodrich & Co. and polyamide elastomeric materials such as, for example, those available under the trademark PEBAX from the Rilsan Company. Generally, any suitable elastomeric fiber forming resins or blends containing the same may be utilized for the nonwoven webs of elastomeric fibers of the invention and any suitable elastomeric film forming resins or blends containing the same may be utilized for the elastomeric films of the invention.

The elastomeric fiber or film forming resin used in the invention may essentially consist of an elastomeric S-EB-S thermoplastic resin which typically may contain plasticizers, pigments, antioxidants and other conventionally employed additives. Further, as discussed above, the S-EB-S block copolymers may be blended with polyolefins, e.g., polyethylene and/or polypropylene. The polyolefin which is utilized in blending the S-EB-S block copolymers must be one which, when blended with the S-EB-S block copolymer and subjected to an appropriate combination of elevated pressure and elevated temperature conditions is extrudable in blended form with the block copolymer. In particular, preferred polyolefin materials include polyethylene, polypropylene and polybutene, including ethylene copolymers, propylene copolymers and butene copolymers. Blends of two or more of the polyolefins may be utilized. A particularly preferred polyethylene may be obtained from U.S.I. Chemical Company under the trade designation Petrothene Na601. (Also referred to as PE Na601 or Na601.) A particularly preferred polypropylene may be obtained from the Himont Corporation under the trade designation PC-973. Characteristics of the U.S.I. Chemical polyethylene are given below in connection with the test runs summarized in the Tables.

Typical characteristics of the Himont PC-973 polypropylene, as stated by Himont, include a density of about 0.900 grams per cubic centimeter measured in accordance with ASTM D 792 and a meltflow rate obtained in accordance with ASTM D 1238, Condition L, of about 35 grams per ten (10) minutes. Other characteristics of the PC-973 are a tensile strength of about 4,300 pounds per square inch (psi) measured in accordance with ASTM D638; a flex modulus of about 182,000 psi measured in accordance with ASTM D 790, B and a Rockwell hardness, R scale, of about 93 measured in accordance with ASTM D 785A. The PC-973 is believed to have a number average molecular weight (Mn) of about 40,100, a weight average molecular weight (Mw) of about 172,000 and a Z average weight (Mz) of about 674,000. The polydispersity of the PC-973 (Mw/Mn) is about 4.29.

Whether the elastic web comprises an elastic film (such as a blown or cast film) or a fibrous elastic web (such as, for example, a nonwoven web of meltblown fibers, or a web of meltblown fibers containing other fibers or particulates which were incorporated into the web during its formation by, for example, utilization of the teachings disclosed in U.S. Pat. No. 4,100,324, discussed above, or a woven or knitted elastic web), it should have sufficient elasticity and be bondable to the gatherable webs of the composite structure of the invention with sufficient strength to form a composite material which may be stretched and relaxed to provide the desired degree of elasticity. Although some of the elastomeric materials, such as those made from KRATON resins, are somewhat tacky, they do not generally exhibit a satisfactorily high degree of adhesion to many materials, particularly when held in an elongated condition while being bonded to the other web or webs of the composite material. Accordingly, heat or other types of conventional bonding techniques should preferably be utilized when such materials are to be utilized in practicing the present invention. It will be appreciated tht the degree of elasticity is one of the important considerations in forming elastic composite fabrics such as those of the present invention, particularly when such composite materials are to be utilized in garments which are designed to conform to the body of the wearer. For example, in the manufacture of disposable diapers a degree of elasticity of the fabric will assist in conforming it to the body contours of the wearer. Further, it is often desired that the composite material should have a soft hand and feel so it is therefore desirable in some cases that the bonding of the elastic web to the other web or webs of the laminate be done without the provision of an adhesive which would tend to make the resultant material stiff.

Because the elastic web may be bonded to a non-elastic material, by which is meant generally any suitable material which lacks the characteristics of an elastic as defined above, the non-elastic material tends to have a limiting effect on the degree of stretch and recovery of the elastic web. For example, if the elastic web is stretched to an elongation of 100 percent, i.e., to twice its relaxed length, and then bonded to a non-elastic web such as a nonwoven polyolefin fiber web, upon release of the stretching force action on the composite web, the non-elastic web tends to prevent the elastic web from retracting fully to its original length. This requires that the elastic limit of the elastic web be greater than the desired minimum elastic limit of the composite material. For example, if it is desired to prepare a composite material stretchable to 100 percent elongation, a 100 cm length of elastic web may be stretched to a length of, for example, 220 cm (120 percent elongation) and bonded at spaced-apart locations to a 220 cm length of non-elastic material. The bonded composite elastic material is then allowed to relax and even if the elastic web is capable of recovering to its original 100 cm length, the non-elastic web bonded thereto will inhibit full recovery and the composite may relax to a length of, say, 110 cm. Puckers or gathers will form in the gatherable web between the bond points. The resulting 110 cm length of composite material is stretchable to its 220 cm length to provide a 100 percent elongatable composite material. The original length of the non-elastic web limits, in this hypothetical example, the attainable elongation of the composite material because the non-elastic web would act as a "stop" to prevent further or excessive stretching of the elastic web under the effect of stretching forces which are less than the failure strength of the non-elastic gathered web.

The elastic web may be bonded to the gatherable web by any suitable means, such as, for example, thermal bonding or ultrasonic welding, which will soften at least portions of at least one of the webs, usually the elastic web, because the elastomeric materials used for forming the elastic web have a lower softening point than many of the materials commonly employed to form the gatherable webs. Thus, effectuating the bonding by applying heat and pressure to the overlaid elastic and gatherable webs will soften at least portions of the elastic web by heating these portions (or the entire elastic web) to at least its softening temperature and applying sufficient pressure to form a reasonably strong and permanent bond between the resolidified softened portions of the elastic web and the gatherable web. One difficulty with such bonding of films or nonwoven elastomeric webs is that the low basis weight of such webs renders them susceptible to losing their ability to contract to their pretensioned, that is prestretched, dimensions if they are subjected, even briefly, to being heated while stretched and allowed to cool in the stretched condition. Such difficulties should not be encountered in dealing with heavy basis weight webs such as elastic foam materials used for carpet backing and the like which should be able to sustain such heating and cooling, at least at localized portions or on the surface thereof, while being maintained under tension for at least a brief period of time without thereafter losing their ability to contract to their pretensioned, that is prestretched, dimensions. However, the elastic films and elastomeric nonwoven webs of elastomeric fibers of the present invention have extremely low basis weights as compared to high basis weight, heavier elastic materials, such as polyurethane foams, which are conventionally stretched and bonded to gatherable webs. For example, the low basis weight elastic webs or elastic films of the present invention may have a basis weight ranging from about 5 grams per square meter to about 300 grams per square meter, preferably from about 5 grams per square meter to about 200 grams per square meter, for example, from about 5 grams per square meter to about 100 grams per square meter. Accordingly, the extreme thinness, that is low basis weight, of the elastic nonwoven webs which may be used in certain embodiments of the invention would appear to preclude subjecting them to such conventional heating and stretching techniques because such materials are subject to losing their ability to contract to their prestretched dimensions if cooled in the stretched condition. Accordingly, loss of the ability of the elastic web to contract to its prestretched dimensions would mean that the gatherable webs would not be gathered upon release of the tensioning, stretching force on the composite web. Thus, the composite web would not possess non-destructive elasticity since any significant stretching of the composite web would result in the gatherable webs being torn or ruptured.

In spite of this apparent problem, a distinct advantage of the present invention is the ability to attain the elastic characteristics in the composite web by bonding a low basis weight elastic web to a gatherable material, such as a non-elastic material, which may be of greater tensile strength than the elastic web, by immediately relaxing the composite after the bonding step. Immediate relaxation of the composite and thus the elastic web after the bonding step allows the elastic web to contract and then cool while relaxed, enabling it to gather the gatherable web so that the composite web possesses elastic properties without rupturing the gatherable webs because the gatherable webs are able to extend and retract with the elastic web as a result of the presence of the gathers. As used herein and in the claims, "immediately" relaxing the elongated composite means relaxing it before the elastic web remains in its elongated condition for a period of time such that it loses its ability to recover at least about 40 percent of its elongation, as described above in defining the term "elastic."

The tensile strength of the finished composite web is in most cases largely determined by the usually stronger non-elastic gatherable web which also serves, as described elsewhere herein, as a "stop" to limit the degree of elongation attainable by the composite web without rupturing of the gatherable web. Naturally, the elastic web must be sufficiently strong to enable it to gather the gatherable web or webs to which it is bonded and, generally, the stiffer the gatherable web or webs are, the stronger must be the recovering force of the elastic web or webs bonded thereto. As used herein and in the claims, a "gatherable" web is one which can be gathered into pleats, loops or the like by contraction of the elastic web or webs bonded to it. Although low basis weight elastic webs are preferred largely for economic reasons, particularly for use in disposable articles, the elastic webs may have basis weights considerably higher than 300 gm/m$^2$, for example, up to about 750 gm/m$^2$ or even higher.

One or more elastic webs may be heat-bonded to one or more gatherable webs, for example, non-elastic webs, by the application of heat and pressure and this may be effectuated by passing the overlaid elastic and gatherable webs, with the elastic web being in a stretched, that is elongated condition, through the nip of a bonder arrangement, at least one of the rollers of the arrangement optionally being heated to impart the requisite bonding temperature to at least the bond sites of one or more of the webs to be bonded. In many cases, the elastic web or webs have softening temperatures which are lower than those of the gatherable web or webs to which the elastic web(s) are to be bonded and, consequently, the elastic web(s) may be the only web(s) which are significantly softened in the bonding step. In other cases, the gatherable web(s) may similarly be softened. Accordingly, the elastic web(s), or the gatherable web(s), or both are thus heated to above the softening temperature of the elastic web, at least at the bond sites therebetween. The heat for the bonding may be applied by the rollers of the bonder arrangement or by another heat source such as a heat source positioned just ahead of the bonder arrangement. However, excellent bonding and an attractive pattern and texture of the composite elastic material is attained by utilizing pattern bonding in which the overlaid stretched elastic and gatherable webs are passed through the nip of a bonder arrangement comprising an anvil roller and a calender roller having a repeating embossing pattern formed thereon. The anvil roller may be smooth or may contain a pattern such as one which is the complementary negative of a positive pattern on the calender roller and one or both of the calendar and anvil rollers may be heated, as mentioned above. One skilled in the art will appreciate that the temperature to which the webs, or at least the bond sites thereof, are heated for heat-bonding will depend not only on the temperature of the heated roll(s) or other heat source but on the residence time of the webs on the heated roll(s) or adjacent the other heat source, the contact pressure, the basis weights of the webs and their specific heats and thermal conductivities. However, for a given combination of webs, and in view of the herein contained disclosure the processing conditions necessary to effectuate satisfactory bonding can be readily determined by one of skill in the art.

As to the bonding pressure utilized in cases where the bonding is effectuated by passing the overlaid webs through the pressure nip of a bonder arrangement having a pair of rolls which form the nip, specification of the overall pressure loading along the nip does not, in itself, take into account complicating factors such as the effects of pressure roll construction, e.g., roller diameters, materials, and embossing patterns, if any, on the nip width and pressure distribution through the nip. Nonetheless, one skilled in the art, taking into account the overall pressure loading along the nip, the materials of construction of the pressure rolls, the pressure roll diameters and the geometry of embossing patterns, if any, on the rolls, will readily be able to appropriately select and vary an effective bonding pressure.

The gatherable web or webs to which one or more of the elastic webs are bonded may themselves be elastic or, more usually, may comprise one or more non-elastic webs. Generally, elastic materials such as elastic fibrous webs have a rubbery feel and in applications where the feel of the composite material is of importance, a non-elastic web such as a bonded carded nonelastic polyester or nonelastic polypropylene fiber web, a spunbonded nonelastic polyester or polypropylene nonelastic fiber web, nonelastic cellulosic fiber webs, e.g., cotton fiber webs, polyamide fiber webs, e.g., nylon 6—6 webs sold under the trademark Cerex by Monsanto, and blends of two or more of the foregoing may be utilized. The production of spunbonded nonwoven webs is illustrated in U.S. Pat. No. 4,340,563, issued July 20, 1982 to David W. Appel et al, the disclosure of which is incorporated by reference herein. Generally, in the spunbonding process a thermoplastic material is extruded through a spinnerette and eduction drawn into filaments to form a coherent web of randomly deposited filaments on a collecting or forming surface. Generally, woven and nonwoven webs of any textile or other material suitable for the purpose may be used. However, relatively inexpensive and attractive composite fabrics with good hand and feel and with good stretchability and recovery characteristics have been attained by bonding to one or both sides of an elastic web (such as a fibrous elastic web) a bonded carded polyester web, a spunbonded polypropylene fiber web, and single and multilayer combinations thereof. Satisfactory results have been attained by pattern bonding the webs together under heat and pressure to provide a composite material with excellent controllable stretchability characteristics and uniform and attractive appearance.

Figure 1:
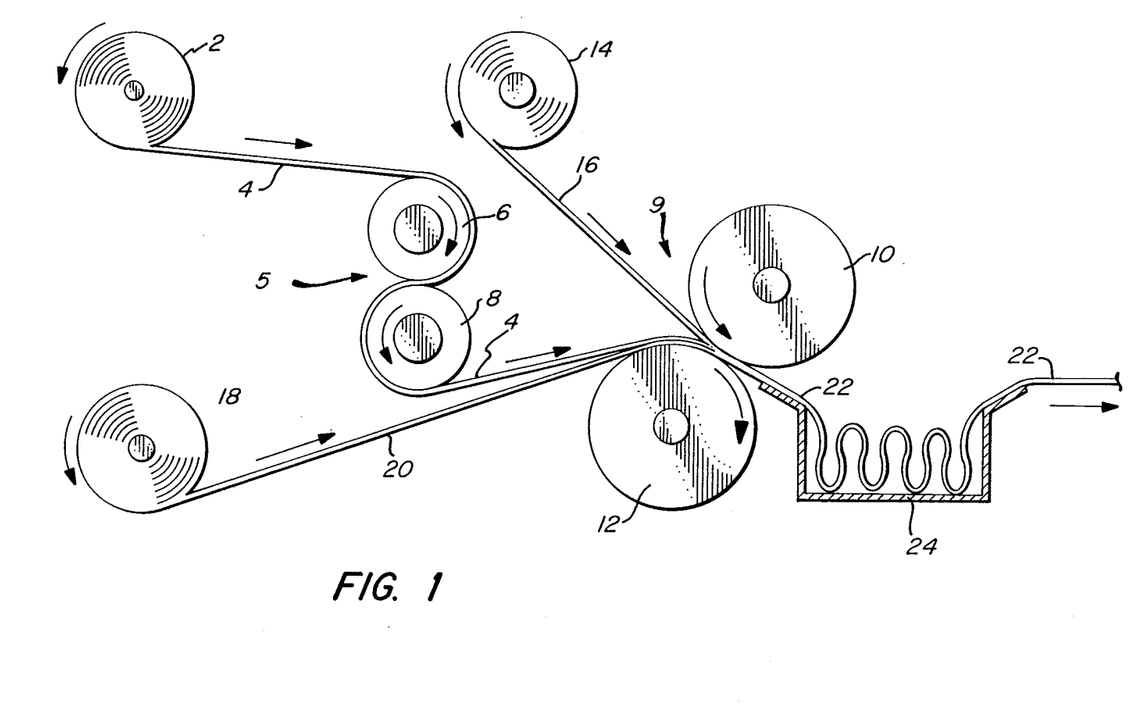
FIG. 1 is a schematic view in elevation illustrating one mode of carrying out the method of the present invention.

Referring now to FIG. 1 of the drawings, there is schematically illustrated a continuous manufacturing process for heat-bonding gatherable webs, which may be non-elastic webs, to each of the two opposite sides of a stretched elastic web. An elastic web which may comprise a fibrous nonwoven elastic web or elastic film 4 is unwound from a supply roll 2 of such fibrous elastic material and, traveling in the direction indicated by the arrows associated therewith, passes through the nip of S roll arrangement 5, comprised of stacked rollers 6, 8, in the reverse-S path indicated by the rotation direction arrows associated with stacked rollers 6 and 8. From S roll arrangement 5, web 4 passes into the pressure nip of a bonder roll arrangement 9, which is comprised of a patterned calender roller 10 and a smooth anvil roller 12. A first gatherable web 16 is unwound from a supply roll 14 and a second gatherable web 20 is unrolled from a supply roll 18. First web 16 and second web 20 travel in the direction indicated by the arrows associated therewith as supply rolls 14 and 18 rotate in the directions indicated by the respective arrows associated therewith. Fibrous elastic web 4 is stretched to a desired percent elongation between S roll arrangement 5 and the pressure nip of bonder roll arrangement 9. By virtue of the fact that the peripheral linear speed of the rollers of S roll arrangement 5 is controlled to be less than the peripheral linear speed of the rollers of bonder roll arrangement 9, web 4 is therefore stretched to a selected percent elongation thereof and maintained in such elongated condition during heat-bonding of the webs 16 and 20 to the web 4 in bonder roll arrangement 9.

One or both of patterned calender roller 10 and smooth anvil roller 12 may be heated and the pressure between these two rollers may be adjusted by well-known means to provide the desired temperature and bonding pressure to bond the webs 16 and 20 to the web 4 and form a composite elastic material 22.

Composite elastic material 22, upon emerging from the pressure nip of bonder roll arrangement 9, passes to a holding box 24 wherein it is maintained in a relaxed, unstretched condition for a length of time sufficient for fibrous elastic web 4 to cool sufficiently to avoid its cooling while it is in a stretched condition and thereby losing all or a considerable proportion of its ability to contract from the stretched dimensions which it had assumed during bonding. It has been found that elastic webs, in particular low basis weight elastic webs such as nonwoven fibrous elastic webs, will lose their ability to contract to or return to their original unstretched dimensions if they are maintained under tension at or above their softening temperature for any significant length of time. A brief recovery period in a relaxed, untensioned condition immediately after bonding has been found to be essential to allow the low basis weight elastic web to contract and gather the gatherable webs so that the bonded web attains its elasticity. After a brief untensioned recovery period of, for example, up to about 30 seconds, e.g., about 3 to 20 seconds, in holding box 24, composite elastic material 22 is withdrawn therefrom for winding up on a storage roll, not shown. The provision of holding box 24 or equivalent means allows the untensioned heat-bonded composite elastic material to stabilize, that is cool, while it is in an untensioned arrangement. This allows the elastic web to contract and gather the gatherable web immediately after bonding of the webs to each other. Additionally, this allows the elastic web to cool in a contracted, that is nontensioned, condition which avoids the elastic web becoming set at the stretched dimensions which it had assumed during bonding. If this were to occur the elastic web would be unable to contract and gather the gatherable web and, accordingly, the composite web would not possess elasticity because any significant stretching of the composite would result in tearing of the gatherable webs.

Conventional drive means and other conventional devices which may be utilized in conjunction with the apparatus of FIG. 1 are well known and, for purposes of clarity, have not been illustrated in the schematic view of FIG. 1.

Figure 2:
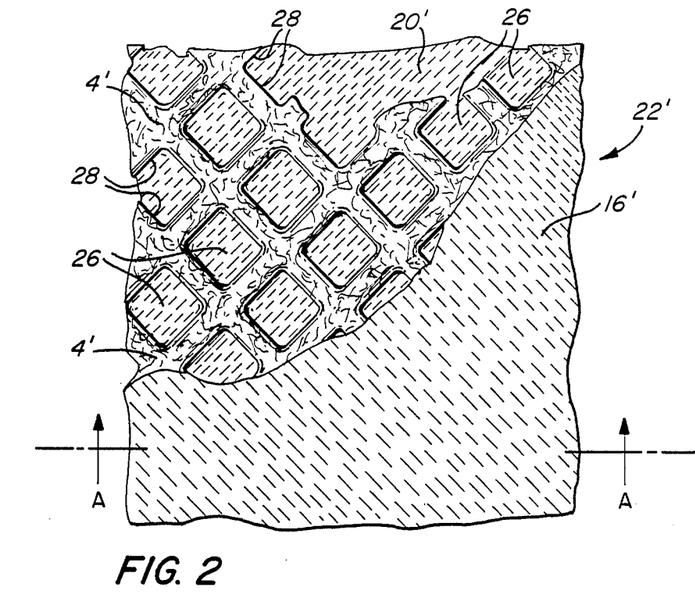
FIG. 2 is a schematic plan view with parts broken away of one embodiment of a composite elastic material in accordance with the present invention, shown in a stretched condition.
Figure 2A:
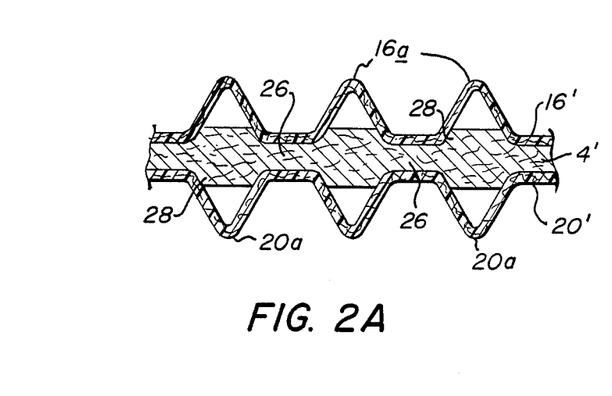
FIG. 2A is a section view along line A—A of FIG. 2, but with the composite elastic material in a relaxed condition relative to its condition in FIG. 2.

Some elastic webs, such as those made of KRATON thermoplastics, e.g., a nonwoven web of meltblown KRATON rubber fibers, have low softening temperatures and yet must be heated sufficiently to attain heat-bonding to what may be a dissimilar material, such as a bonded carded polyester web. For example, KRATON G block copolymer used to make some of the elastic materials of the present invention softens at about 65° C. Successful heat-bonding of such dissimilar materials may be attained with a patterned, i.e., embossing, calender roller in which the raised portions of the pattern impose sufficient heat and pressure upon the overlaid gatherable web and stretched elastic web such that the fine fibers of the elastic web are softened to the extent that they may be melted and, depending upon the temperature of embossing and the compressive embossing force imposed upon the webs by the bonder roller arrangement, may be forced from the areas of the elastic web which are compressed by the raised portions of the embossing pattern, resulting in a pattern of fine holes in the elastic web. If the temperature and pressure of embossing is not such that the fine holes are formed, the elastic web will usually be, as a result of its softening during embossing, indented in the area of embossing. In cases where holes are present in the elastic web, the peripheries of the holes in the elastic web appear to be formed of resolidified or otherwise condensed portions of the material of the elastic web which portions appear to be bonded quite well to the web or webs of gatherable material. For example, with reference to FIGS. 2 and 2A there is shown (schematically and not necessarily to scale, including relative thicknesses of the layers and size of the embossed areas or indentations 30) a composite material 22' made by passing overlain webs 16', 4' and 20' through the pressure nip between calender roller 10 and the anvil roller 12. The composite material 22' is comprised of a first gatherable web 16' and a second gatherable web 20' heat-bonded to respective opposite sides of a fibrous elastic web 4'. The bond sites are spaced-apart, resulting in gathers or pleats 16a and 20a (FIG. 2A) being formed in webs 16' and 20' when the composite material 22' is in a relaxed condition as shown in FIG. 2A. Gathers 16a and 20a are not shown in FIG. 2 in order to be suggestive of the appearance of the composite material 22' in its stretched condition. Fibrous elastic web 4' has a plurality of embossed areas 26 formed therein corresponding to the raised portions of a repeating diamond embossing pattern on the calender roller 10. The temperature and pressure maintained in the nip between the embossing calender roller 10 and anvil roller 12 was such that the pressure and temperature imposed by the raised portions of calender roller 10 formed indentations 30 within fibrous elastic web 4' by softening or melting the microfibers of the web 4'. The peripheral portions 28 of the indentations 30 of the web 4' illustrated in FIG. 2A include a resolidified portion of the material which was formerly located in the indented area 30 of fibrous elastic web 4'. Peripheral portions 28, upon resolidification after softening or melting in the pressure nip of calender roller 10 and anvil roller 12, tend to form a reasonably strong bond with the overlaid gatherable webs 16' and 20'. In examining samples of the elastic composite, the indentations 30 became visible only after peeling away one of the gatherable webs 16' or 20'. In several situations peeling away of one or more of the gatherable webs revealed that holes were formed through the elastic web in the embossed areas 26. However, it is possible that a thin layer, that is a highly indented area, of material of elastic web 4' extending within the area of the holes was stripped away with the gatherable web upon the peeling away of the gatherable web from the elastic web. That is, the holes may have been formed as a result of the stripping away step as opposed to the embossing step. Particularly with heavier basis weight elastic webs, the embossing may result in a waffle-like pattern in which indentations as opposed to holes are present in the elastic web.

A series of tests was run in which gatherable webs of different materials were heat-bonded in a similar fashion to a nonwoven elastic web comprising meltblown fibers of a blend of KRATON (Shell Chemical Company) rubber and polyethylene. The runs were carried out on apparatus of a type schematically illustrated in FIG. 1 comprising a bonder arrangement (corresponding to 9 in FIG. 1) having a 14 inch (35.6 cm) wide bonding surface provided by a nominal 7 inch (17.8 cm) diameter smooth stainless steel anvil roller (corresponding to 12 in FIG. 1) and a nominal 7 inch (17.8 cm) diameter stainless steel calender roller (corresponding to 10 in FIG. 1) having thereon a raised diamond embossing pattern comprised of squares both diagonally aligned and diagonally oriented relative to the machine direction of the web. The embossing pattern is comprised of lands raised 0.09 inch (0.229 cm) above the roller base surface, each land being a square having sides 1/16 of an inch (0.159 cm) long with the facing sides of adjacent squares being ⅛ of an inch (0.318 cm) apart as measured perpendicularly to and between adjacent sides.

The calender and anvil rollers are independently oil-heated and there is an S roll (corresponding to 5 in FIG. 1) and suitable feed rolls (corresponding to 2, 14 and 18 in FIG. 1) to feed the webs to the bonder roll at controlled speeds. When composite elastic materials were made in which only one side of the fibrous elastic web was laminated to a gatherable web, the supply roll corresponding to supply roll 18 of FIG. 1 was eliminated so that the gatherable web passed over the embossing calender roller 10 and the fibrous elastic web passed over the smooth anvil roller 12 as illustrated in the schematic representation of FIG. 1. Both the embossing calender roller 10 and smooth anvil roller 12 were heated to the temperatures indicated below. The net force urging anvil roller 12 and calender roller 10 towards each other in the runs described below was about 3,400 pounds (1,542 Kg) plus or minus about ten percent, which is thus the force acting on the overlaid webs passing therethrough as no nip gap-limiting devices were utilized. The elastic web widths were 12 inches (30.5 cm) wide before elongation and varied from about 10½ inches (26.7 cm) wide at about 25 percent elongation ("E" in the Tables below) to about 7 inches (17.8 cm) wide at about 550 percent elongation.

The gatherable materials utilized in runs 1-18 are summarized in Table I. Table II and those following show the temperature of the anvil and calender rollers, the basis weight of the fibrous elastic web utilized, the linear speed of the webs in the respective pinches of the bonder roll 9 and S roll 5 and the consequent percent elongation imposed on the fibrous elastic web during bonding. In each case, elastic meltblown fibers comprised a blend of 60 parts by weight KRATON GX 1657 block copolymer and 40 parts by weight of a polyethylene sold under the trade designation Petrothene Na601 by the U.S.I. Chemical Company. (Also referred to as PE Na601 or Na601.) KRATON GX 1657 rubber is described in detail above.

Information obtained from U.S.I. Chemical Company states that the Na601 is a low molecular weight, low density polyethylene for application in the areas of hot melt adhesives and coatings. U.S.I. has also stated that the Na601 has the following nominal values: (1) a Brookfield Viscosity, cP at 150 degrees Centigrade of 8500 and at 190 degrees Centigrade of 3300 when measured in accordance with ASTM D 3236; (2) a density of 0.903 grams per cubic centimeter when measured in accordance with ASTM D 1505; (3) an equivalent Melt index of 2,000 grams per ten minutes when measured in accordance with ASTM D 1238; (4) a ring and ball softening point of 102 degrees Centigrade when measured in accordance with ASTM E 28; (5) a tensile of 850 pounds per square inch when measured in accordance with ASTM D 638; (6) an elongation of 90 percent when measured in accordance with ASTM D 638; (7) a modulus of Rigidity, $T_F$ (45,000) of $-34$ degrees Centigrade and (8) a penetration Hardness, (tenths of mm) at 77 degrees Fahrenheit of 3.6.

Na601 polyethylene is believed to have a number average molecular weight (Mn) of about 4,600; a weight average molecular weight (Mw) of about 22,400 and a Z average molecular weight (Mz) of about 83,300. The polydispersity (Mw/Mn) of the Na601 is about 4.87.

TABLE I

| | Gatherable Webs | |
|---|---|---|
| Runs | Material | Basis Weight |
| 1-3 | Thermally bonded, carded web of poly(ethylene terephthalate) fibers | 22 gms/yd² |
| 4-8 | Multi-layer carded web comprising a layer of 60% by weight poly (ethylene terephthalate) fibers and 40% by weight polypropylene fibers (fluffy side) sonically bonded to a layer of spunbonded polypropylene fibers. | 70 gms/m² |
| 9-11 | Spunbonded polypropylene fiber | 0.4 oz/yd² |
| 12-15 | Spunbonded polypropylene fiber | 0.7 oz/yd² |
| 16-17 | Spunbonded polypropylene fiber | 0.4 oz/yd² |
| 18 | Thermally bonded, carded web of poly(ethylene terephthalate) fibers | 22 gms/yd² |

The following legends apply to Tables II, III, IV, V and VI

Anvil T12=Temperature of Anvil Roller (12), degrees Centigrade

Calender T10=Temperature of Calender Roller (10), degrees Centigrade

BW=Basis Weight of Elastic Web (4), gram per square meter

Web LS=Respective Linear Speeds of Webs passing through Bonder Roll (9)/S Roll (5), feet per minute %E=Percent Elongation of Elastic Web (4) at Bonding (Rounded to nearest integer)

NOTE: With reference to the schematic diagram of FIG. 1, bonder roll (9) is comprised of anvil roller (12) and calender roller (10). S roll (5) is comprised of rolls (6) and (8).

TABLE II

| Run | Anvil T12 | Calender T10 | BW | Web LS | % E |
|---|---|---|---|---|---|
| 1 | 54 | 85-86 | 125 | 20/10 | 100 |
| 2 | 54 | 85-86 | 125 | 20/8 | 150 |
| 3 | 52 | 88 | 125 | 21/7 | 200 |
| 4 | 52 | 96-99 | 125 | 20/10 | 100 |
| 5 | 52 | 96-99 | 125 | 20/8 | 150 |
| 6 | 52 | 96-99 | 125 | 21/7 | 200 |
| 7 | 52 | 96-99 | 65 | 21/7 | 200 |
| 8 | 52 | 96-99 | 65 | 20/10 | 100 |
| 9 | 52 | 96 | 125 | 20/10 | 100 |
| 10 | 52 | 96 | 125 | 20/8 | 150 |
| 11 | 52 | 96 | 125 | 21/7 | 200 |
| 12 | 52 | 96 | 125 | 21/7 | 200 |
| 13 | 52 | 85 | 125 | 21/7 | 200 |
| 14 | 52 | 85 | 125 | 20/10 | 100 |
| 15 | 52 | 85 | 125 | 20/8 | 150 |
| 16 | 52 | 85 | 125 | 21/7 | 200 |
| 17 | 52 | 85 | 125 | 21/7 | 200 |

TABLE II-continued

| Run | Anvil T12 | Calender T10 | BW | Web LS | % E |
|---|---|---|---|---|---|
| 18 | 82 | 85-88 | 65 | 21/6 | 250 |

All of the runs except Run 18 applied the gatherable web to one side only of the fibrous elastic web. In Run 18 the gatherable web was applied to both sides of the fibrous elastic web.

The product obtained in Runs 1 through 3 showed very good elasticity and appearance, the gatherable web side being puckered in a fine, regular repeating pattern. The product of Runs 4 through 6, in which the fluff side of the multi-layer gatherable web was bonded to the fibrous elastic web showed good appearance and good elasticity with good bonding strength. The product produced in Run 7 showed large, irregular puckers and weak bonding and was generally considered to be unsatisfactory. The products of Runs 8 and 9 showed good appearance and good elasticity. The product of Run 10 showed some holes in the elastic and the product of Run 11 showed many holes in the elastic, indicating that the bonding temperature may have been too high. Run 12 was unsuccessful in that the fibrous web broke after bonding was started and rather low bonding strengths were attained. In Run 13, the elastic did not break during bonding but the product delaminated. Runs 14 and 15 were more successful, producing a product with good appearance and elasticity but with poor bonding strength, the products tending to delaminate rather easily. Runs 16 and 17 were not successful in that the fibrous elastic material broke when bonding was started. Run 18 was successful and an attractive product with adequate bonding strength was attained.

A further series of runs was carried out in an attempt to produce composite elastic material having elongations of approximately 25 percent, 50 percent, 75 percent and 100 percent before failing. Failure occurs at the "ultimate elongation" of the material which is the elongation at which the material tears or otherwise fails. Elongation was tested in an Instron testing device. A two inch by five inch rectangle of the material was cut with the five inch long sides being substantially parallel to the machine direction of the web of composite material from which the sample was cut, and the two inch sides were clamped in the jaws of a properly calibrated Instron testing device. It was then attempted to elongate each sample in two stages, with one minute's rest between stages, to elongations of 50 percent and then 100 percent, after which the sample was relaxed to zero elongation. If the sample fails during either of these two stages, the percent elongation at failure is the "ultimate elongation." If the sample did not fail during either of these two stages, it was, after being relaxed to zero elongation, then stretched at 10 feet per minute until it failed, the percent elongation at break or tear being the "ultimate elongation." The desired or target elongation of 25 percent, 50 percent, etc., of the composite elastic material should not be confused with the definition given above of an elastic material as one which is in itself (not the composite) capable of at least 25 percent elongation and a stated degree of recovery. The stiffness, basis weight and bonding pattern of the gatherable web or webs bonded to the elastic web or webs can be controlled in order to affect (reduce) the degree of elongation of the composite material. For example, composite materials of considerably less than 100 percent elongation are often desired for certain end uses.

The composite elastic materials used in Runs 19-26 were made by utilizing fibrous elastic webs of the same KRATON GX 1657-polyethylene Na601 60/40 blends as utilized in Runs 1-18 and bonding to each side of the fibrous elastic web either a 22 grams per square yard poly (ethylene terephthalate) bonded carded web material made by Carolina Formed Fabrics (Runs 19-24) or a one ounce per square yard spunbonded poly(ethylene terephthalate) fiber web sold by E. I. DuPont de Nemours and Company under the registered trademark REEMAY (Runs 25 and 26). The results of these runs are set forth in Table III following.

TABLE III

| Run | Anvil T12 | Calender T10 | BW | Web LS | % E |
|---|---|---|---|---|---|
| 19 | 77 | 74 | 50 | 20/7 | 186 |
| 20 | 74 | 74 | 50 | 20/10 | 100 |
| 21 | 74 | 74 | 50 | 20/12-13 | 67-54 |
| 22 | 74 | 74 | 50 | 20/16 | 25 |
| 23 | 73 | 74 | 50 | 24/16 | 50 |
| 24 | 74 | 76 | 50 | 24/16 | 50 |
| 25 | 74 | 76 | 65 | 20/13 | 54 |
| 26 | 86 | 84 | 65 | 20/13 | 54 |

See legends preceding Table II

The composite elastic material product of Run 19 was generally satisfactory but seemed to be somewhat overbonded, the sample of the composite material produced showing approximately 100 percent elongation. Accordingly, the anvil roller temperature was reduced somewhat for run 20 which produced a satisfactory composite material product showing an ultimate elongation of about 100 percent. The product obtained in Run 21 showed very good uniformity. Run 22 produced satisfactory product showing a percent ultimate elongation of 56 percent. Run 23 was carried out using three different lots of fibrous elastic web material, the first two lots of which yielded composite elastic material products having ultimate elongations of 86 percent and the third lot yielding product showing an ultimate elongation of 76 percent.

In Run 25, the one ounce per square yard spunbonded REEMAY poly(ethylene terephthalate) fiber web was used on the calender roller side of the fibrous elastic web and a 0.7 ounce per square yard basis weight web of the same material was used on the smooth, anvil roller side of the fibrous elastic web. Run 25 produced good bonding and a satisfactory composite elastic material product which was somewhat stiffer that that obtained with the Carolina Formed Fabrics poly(ethylene terephthalate) bonded carded web material.

Run 26 is a repeat of Run 25 except utilizing somewhat higher bonding temperatures as indicated. The REEMAY spunbonded poly(ethylene terephthalate) fiber web material bonded very well at the higher temperature. However, at such higher bonding temperatures it might be better to utilize a somewhat heavier basis weight fibrous elastic web although a satisfactory composite elastic material was obtained in this run.

The necessity of allowing the composite web to relax immediately after bonding was demonstrated by comparative test Runs 27 and 28, in which similar conditions were maintained except for omission of the relaxation step in Run 27. For these runs, a 22 grams per square yard thermally bonded poly(ethylene terephthalate) fiber nonwoven web was bonded to each side of a nonwoven fibrous web of fibers of the same KRATON GX 1657-polyethylene Na601 60/40 blend as was utilized in Runs 1-18 and 19-26, having a basis weight as shown in Table IV, which sets forth the data for Runs 27 and 28.

TABLE IV

| Run | Anvil T12 | Calender T10 | BW | Web LS | % E |
|---|---|---|---|---|---|
| 27 | 110 | 110 | 60 | 20/5-6 | 233-300 |
| 28 | 110 | 110 | 85 | 18/6-7 | 157-200 |

See legends preceding Table II

In Run 27, the bonded composite material was maintained under tension after the bonding step by winding it directly onto a storage roll as the composite material emerged from the bonder rolls, without allowing it to relax. With respect to FIG. 1, this effectively involved replacing holding box 24 with a driven take-up roll. The resultant composite web had substantially no non-destructive elasticity because its elastic web component, as a result of the fact that the elastic web was held in an elongated, tensioned condition while it cooled after bonding, had lost its ability to contract and thus form gathers in the gatherable webs. By non-destructive elasticity is it meant that the composite could be stretched and allowed to contract without rupturing the gatherable webs. Accordingly, it should be noted that the elastic web, upon removal of the gatherable webs therefrom, still possessed elasticity in that it could be stretched and would contract to the dimensions which it had assumed during bonding, but would not contract back to its original prebonding unstretched dimensions. As a result of this, the composite web did not possess non-destructive elasticity because the gatherable webs would have been ruptured or torn in order to stretch the composite beyond the dimensions it possessed during bonding. Accordingly, the composite web could not be elongated without tearing of the gatherable webs and thus the gatherable webs resisted such elongation. Because the elastic web had lost its ability to contract and form gathers in the gatherable webs, the composite web had a smooth, nongathered appearance. Run 28 was similar to Run 27 except that the composite was allowed to run freely off the bonder rolls and the elastic web contracted, forming gathers in the non-elastic web and providing an attractive, elastic composite web.

A further series of runs was conducted in which elastic webs of meltblown KRATON GX 1657-polyethylene Na601 fibers of the same 60/40 blend as utilized in Runs 1-18 were bonded on each of their opposite sides to a poly(ethylene terephthalate) powder bonded carded web of a basis weight of 14 grams per square yard, sold by Carolina Formed Fabrics under the trademark CARELLE. (The bonding powder used in the CARELLE fabric is sold by Eastman Chemical Products Inc. as FA 252 polyester powder). The fibrous elastic web in each of the following Runs 29-40 had a basis weight of 55 grams per square meter. After the two-side bonded composite elastic materials were made, six specimens were taken from each run, the specimens being cut three inches wide in the cross direction and seven inches long in the machine direction. For three of the specimens from each run, one of the poly(ethylene terephthalate) webs (Side 1) was separated for a distance of approximately one inch along the machine direction of the specimen and placed in one jaw of an Instron tester while the remaining two bonded layers were placed in the opposite jaw of the tester which was then set to move the jaws apart at a rate of 10 inches (25.4 cm) per minute. The three highest peaks registered for at least four inches (10.2 cm) of specimen delamination were noted and an average taken of the nine values thus obtained for three specimens, giving a force in grams, per three inch width of specimen, required to delaminate the poly(ethylene terephthalate) web (Side 1) from the fibrous elastic web. For the three remaining specimens from each run, the poly(ethylene terephthalate) web on Side 2 of the composite elastic material (Side 2 being the side opposite to Side 1 above) was separated for a distance of approximately one inch along the machine direction of the specimen and placed in one jaw of an Instron tester while the remaining two bonded layers were placed in the opposite jaw of the tester which was then set to move the jaws apart at a rate of 10 inches (25.4 cm) per minute. The three highest peaks registered for at least four inches (10.2 cm) of each specimen delamination were noted and an average taken of the nine values thus obtained for the three specimens, giving a force in grams, per three inch width of specimen, required to delaminate the poly(ethylene terephthalate) web (Side 2) from the fibrous elastic web.

The results are set forth in the following Table V, to which, in addition to the table headings defined above, the following applies:

Bond Strength=Bond strength expressed as the force, in grams, required to peel away a three-inch wide strip of gatherable web from the elastic web to which it is bonded, measured as described above.

TABLE V

| Run | Anvil T12 | Calender T10 | Web LS | % E | Bond Strength Side 1 | Bond Strength Side 2 |
|---|---|---|---|---|---|---|
| 29 | 67 | 63 | 28/8 | 250 | 76 | 101 |
| 30 | 64 | 65 | 56/16 | 250 | 84 | 125 |
| 31 | 64 | 64 | 28/7 | 300 | 59 | 64 |
| 32 | 64 | 64 | 56/14 | 300 | 61 | 74 |
| 33 | 72 | 71 | 28/8 | 250 | 106 | 156 |
| 34 | 72 | 73 | 56/16 | 250 | 78 | 114 |
| 35 | 72 | 73 | 28/7 | 300 | 104 | 115 |
| 36 | 72 | 73 | 56/14 | 300 | 94 | 120 |
| 37 | 77 | 78 | 28/8 | 250 | 170 | 253 |
| 38 | 76 | 78 | 56/16 | 250 | 129 | 143 |
| 39 | 76 | 78 | 56/14 | 300 | 130 | 240 |
| 40 | 77 | 78 | 28/7 | 300 | 171 | 279 |

See legends preceding Table II

Similar additional bonding strength tests were conducted substituting for the diamond patterned embossing calender roller a calender roller having a repeating regular pattern of six circular dots arranged in hexagonal patterns between which triangular patterns of three circular dots are interspersed. The raised dots comprise about 17 percent of the surface area of the embossing roll. Generally, similar conditions were otherwise maintained and comparable bonding strength results were obtained although the diamond embossing pattern overall appeared to provide somewhat higher bonding strengths than the hexagonal/triangular pattern of circular dots.

Another series of runs was conducted in which a cast elastic film of about one mil thickness was made from a blend comprising 85 percent by weight of a resin sold under the trademark POLYTROPE 37701 by A. Schulman Corporation of Akron, Ohio and 15 percent by weight of AMPACET White Concentrate, comprising polypropylene and titanium dioxide, sold by Ampacet Corporation of Mt. Vernon, N.Y. The film was bonded to a bonded carded web of poly(ethylene terephthalate) having a basis weight of 22 grams per square yard. Polytrope resin is believed to be a block copolymer of poly(cis-butadiene) and poly(t-butyl-methyacrylate). The conditions which were utilized are set forth in Table VI, below.

TABLE VI

| Run | Anvil T12 | Calender T10 | Web LS | % E |
|-----|-----------|--------------|--------|-----|
| 41  | 110       | 107          | 20/8   | 150 |
| 42  | 110       | 107          | 20/10  | 100 |

See legends preceding Table II

In each of Runs 41 and 42, a product was obtained which had good appearance and was not very noisy with respect to crackling of the film when the composite material was crumpled in the hand. The product of Run 41 showed more stretch than that of Run 42 as would be expected from the greater degree of elongation of the elastic film during bonding. Other elastic films may of course be used; for example, a film may be made of KRATON GX 1657 thermoplastic and a polyolefin composition identical or similar to the compositions described above for use in meltblowing to make webs of nonwoven microfibers. Such elastic films are also useful in the practice of the invention.

Tests with other elastomeric materials were carried out in which a sample of the elastic web was stretched by hand and hand fed into the bonder arrangement together with the gatherable webs. For example, an elongated elastic web of meltblown fibers of polyurethane sold under the trademark ESTANE (B. F. Goodrich & Co.) was heat-bonded on both sides to the same poly(ethylene terephthalate) fiber powder bonded carded web used in Runs 29–40. In similar fashion, a (90 gram per square meter basis weight) elongated elastic web of meltblown fibers on an elastomeric polyester sold under the trademark HYTREL (E. I. DuPont DeNemours & Co.) was heat-bonded on both sides to the same poly(ethylene terephthalate) fiber powder bonded carded web. The composite made with the polyurethane elastic web showed good stretch and an attractive appearance with significant necking-down of the product due to the fact that the sample of the elastic web was hand fed to the bonder arrangement by holding the sample in a machine direction stretched condition and allowing the sample to feed through the bonder arrangement. The composite made with the polyester elastic web showed fairly good bonding, with apparently better stretch in the cross direction than in the machine direction.

Composite elastic materials of the invention are utilizable generally in any article calling for an elastic material such as, but not limited to, stretchable protective covers and wraps, outerwear, undergarments, menstrual and incontinence control articles and garments such as disposable diapers, and the like. Their low cost relative to woven or knitted fabrics permits economic adaptations to "disposable" articles, by which is meant articles intended to be disposed of, rather than laundered and re-used, after one or a few uses.

This case is one of a group of cases which were filed on the same date. The group includes U.S. Pat. No. 4,657,802 which issued on Apr. 14, 1987 in the name of M. T. Morman and entitled Composite Nonwoven Elastic Web; U.S. Pat. No. 4,652,487 which issued on Mar. 24, 1987 in the name of M. T. Morman entitled Gathered Fibrous Nonwoven Web; U.S. Pat. No. 4,663,220 which issued on May 5, 1987 in the name of M. T. Morman and T. J. Wisneski entitled Polyolefin-Containing Extrudable Compositions and Methods For Their Formation Into Elastomeric Products; U.S. Pat. No. 4,655,760 which issued on Apr. 7, 1987 in the name of M. T. Morman and T. J. Wisneski entitled Elasticized Garment and Method of Making the Same; U.S. Pat. No.4,692,371 which issued on Sept. 8, 1987 in the name of M. T. Morman and T. J. Wisneski entitled High Temperature Method of Making Elastomeric Materials and Materials Obtained Thereby; application Ser. No. 06/760,437 in the name of M. J. Vander Wielen and J. D. Taylor entitled Composite Elastomeric Material and Process for Making the Same; and application Ser. No. 06/760,691 in the name of W. B. Haffner, M. T. Morman and T. J. Wisneski entitled Block Copolymer-Polyolefin Elastomeric Films. The subject matter of all of these applications is hereby incorporated by reference.

While the invention has been described in detail with respect to specific preferred embodiments thereof, it will be appreciated that upon a reading and understanding of the foregoing numerous variations will occur to those skilled in the art which variations are believed to lie within the scope and spirit of the present invention and the appended claims.

What is claimed is:

1. A method of producing a composite elastic material comprising the steps of:
   elongating a nonwoven fibrous elastic web having a basis weight of from about 5 to about 300 grams per square meter;
   joining the elongated nonwoven fibrous elastic web at spaced-apart locations to at least one gatherable web;
   relaxing the elongated nonwoven fibrous elastic web whereby the gatherable web is gathered between said spaced-apart locations.

2. The method of claim 1 wherein the nonwoven fibrous elastic web has a basis weight of from about 5 to about 200 grams per square meter.

3. The method of claim 1 wherein the nonwoven fibrous elastic web has a basis weight of from about 5 to about 100 grams per square meter.

4. The method of claim 1 wherein the nonwoven fibrous elastic web is joined to the gatherable web under conditions which soften said spaced-apart locations of said nonwoven fibrous elastic web and the nonwoven fibrous elastic web is relaxed immediately after the joining step.

5. The method of claim 1 wherein the nonwoven fibrous elastic web includes microfibers having a diameter not greater than about 100 microns.

6. The method of claim 1 wherein the nonwoven fibrous elastic web includes microfibers having a diameter of from about 1 to about 50 microns.

7. The method of claim 4 wherein the nonwoven fibrous elastic web is joined to the gatherable web at a temperature of from about 65° C. to about 120° C.

8. The method of claim 4 wherein the nonwoven fibrous elastic web is joined to the gatherable web at a temperature of from about 70° C. to about 90° C.

9. The method of claim 1 or claim 5 wherein the nonwoven fibrous elastic web is comprised of an A-B-A' block copolymer wherein A and A' are the same or different thermoplastic polymer block, and wherein B is an elastomeric polymer block.

10. The method of claim 9 wherein A and A' each is a thermoplastic styrenic moiety and B is selected from the group consisting of poly(ethylene-butylene), polyisoprene and polybutadiene.

11. The method of claim 10 wherein B is poly(ethylene-butylene).

12. The method of claim 10 wherein each of A and A' is selected from the group consisting of polystyrene and polystyrene homologs.

13. The method of claim 12 wherein B is poly(ethylene-butylene).

14. The method of claim 1 or claim 5 wherein the gatherable web comprises a nonwoven, non-elastic material.

15. The method of claim 10 wherein the sum of the molecular weight of A plus the molecular weight of A' comprises from about 14 to 31 percent of the molecular weight of the A-B-A' block copolymer.

16. The method of claim 11 wherein the sum of the molecular weight of A plus the molecular weight of A' comprises from about 14 to 29 percent of the molecular weight of the A-B-A' block copolymer.

17. The method of claim 13 wherein the nonwoven fibrous elastic web is comprised of a blend of said block copolymer plus a polyolefin.

18. The method of claim 17 wherein the polyolefin is selected from the group consisting of one or more of polyethylene, polypropylene, polybutene, ethylene copolymers, propylene copolymers and butene copolymers.

19. The method of claim 1 or claim 5 wherein the nonwoven fibrous elastic web is joined to the gatherable web by passing the elastic and gatherable webs in an overlaid configuration through a pressure nip formed between a pair of bonding rolls, at least one of said rolls comprising a patterned calender roller and at least one of said rolls being heated to a temperature above the softening temperature of the nonwoven fibrous elastic web.

20. The method of claim 1 or claim 5 including maintaining the nonwoven fibrous elastic web in a stretched condition at of at least about 100 percent elongation during the joining.

21. The method of claim 1 or claim 5 wherein the gatherable web comprises a non-elastic web.

22. The method of claim 5 including maintaining the nonwoven fibrous elastic web in a stretched condition of at least about 25 percent elongation during the joining.

23. The method of claim 5 including maintaining the nonwoven fibrous elastic web in a stretched condition of from about 25 percent to 550 percent during the joining.

24. The method of claim 22 wherein the nonwoven fibrous elastic web has a basis weight of from about 5 to about 200 grams per square meter.

25. The method of claim 22 wherein the gatherable web comprises a nonwoven, non-elastic web.

26. The method of claim 1 or claim 5 including bonding a non-elastic web to each of the opposite sides of the nonwoven fibrous elastic web.

27. The method of claim 1 or claim 5 wherein the nonwoven fibrous elastic web is relaxed for a period up to about 30 seconds after joining.

28. An elastic composite material comprising at least one nonwoven fibrous elastic web having a basis weight of from about 5 to about 300 grams per square meter joined at spaced-apart locations to at least one gatherable web, said gatherable web being gathered between said spaced-apart locations.

29. The material of claim 28 wherein the nonwoven fibrous elastic web has a basis weight of from about 5 to about 200 grams per square meter.

30. The material of claim 28 wherein the nonwoven fibrous elastic web has a basis weight of from about 5 to about 100 grams per square meter.

31. The material of claim 28 wherein the nonwoven fibrous elastic web includes microfibers having a diameter of not greater than about 100 microns.

32. The material of claim 28 wherein the nonwoven fibrous elastic web includes microfibers of from about 1 to about 50 microns in diameter.

33. The material of claim 28 wherein the nonwoven fibrous elastic web comprises a nonwoven web of meltblown elastomeric fibers selected from the group consisting of (i) fibers of A-B-A' block copolymers wherein A and A' may be the same or different thermoplastic polymer block and B is an elastomeric polymer block, and (ii) fibers of blends of one or more polyolefins with A-B-A' block copolymers wherein A and A' each is a styrenic moiety and B is poly(ethylene-butylene).

34. The material of claim 33 wherein each of A and A' is selected from the group consisting of polystyrene and polystyrene homologs, and the polyolefin is selected from the group consisting of one or more of polyethylene, polypropylene, polybutene, ethylene copolymers, propylene copolymers and butene copolymers.

35. The material of claim 33 wherein each of A and A' is selected from the group consisting of polystyrene and polystyrene homologs and the sum of the molecular weight of A plus the molecular weight of A' is from about 14 to 29 percent of the molecular weight of the A-B-A' block copolymer.

36. The material of claim 34 wherein the block copolymer comprises at least about 10% by weight of the fibers.

37. The material of claim 34 wherein the block copolymer comprises at least about 20% by weight of the fibers.

38. The material of claim 34 wherein the block copolymer comprises at least about 30% by weight of the fibers.

39. The material of claim 34 wherein the fibers are comprised of from about 10 percent to 90 percent by weight of the A-B-A' block copolymer and from about 90 percent to 10 by weight of the polyolefin.

40. The material of claim 28 or claim 31 wherein the nonwoven fibrous elastic web is joined to the gatherable web at a plurality of spaced-apart locations in a repeating pattern.

41. The material of claim 40 wherein the gatherable web is a nonwoven, non-elastic material.

42. The material of claim 41 wherein the gatherable web comprises a web of fibers selected from the group consisting of polyester fibers, polyolefin fibers, polyamide fibers, cellulosic fibers and mixtures of two or more thereof.

43. The material of claim 41 wherein the gatherable web comprises a nonwoven web of poly(ethylene terephthalate) fibers.

44. An elastic composite material comprising at least one nonwoven fibrous elastic web having a basis weight of from about 5 to about 300 grams per square meter, said nonwoven fibrous elastic web including microfibers having a diameter of not greater than about 100 microns and being joined, at spaced-apart locations, to at least one gatherable web, said gatherable web being gathered between said spaced-apart locations.

* * * * *